United States Patent
Erva et al.

(10) Patent No.: US 7,742,888 B2
(45) Date of Patent: *Jun. 22, 2010

(54) ALLOCATING PROCESSING UNITS TO GENERATE SIMULATED DIFFRACTION SIGNALS USED IN OPTICAL METROLOGY

(75) Inventors: Hemalatha Erva, Fremont, CA (US); Hong Qiu, Union City, CA (US); Junwei Bao, Palo Alto, CA (US); Vi Vuong, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 829 days.

This patent is subject to a terminal disclaimer.

(21) Appl. No.: 11/493,290

(22) Filed: Jul. 25, 2006

(65) Prior Publication Data

US 2008/0027565 A1      Jan. 31, 2008

(51) Int. Cl.
    *G01N 37/00* (2006.01)
(52) U.S. Cl. .................................................. 702/81
(58) Field of Classification Search ............. 702/81, 702/82, 83, 84, 94, 127, 189; 356/600–636; 700/95, 96, 121; 348/14; 438/14, 16
See application file for complete search history.

(56) References Cited

U.S. PATENT DOCUMENTS

| | | | |
|---|---|---|---|
| 6,353,769 B1 * | 3/2002 | Lin | ........................... 700/101 |
| 6,785,638 B2 | 8/2004 | Niu et al. | |
| 6,891,626 B2 | 5/2005 | Niu et al. | |
| 6,943,900 B2 | 9/2005 | Niu et al. | |
| 7,330,279 B2 * | 2/2008 | Vuong et al. | ................. 356/625 |
| 7,394,554 B2 * | 7/2008 | Vuong et al. | ................. 356/625 |
| 2004/0017574 A1 * | 1/2004 | Vuong et al. | ................. 356/625 |
| 2004/0267397 A1 | 12/2004 | Doddi et al. | |
| 2005/0209816 A1 | 9/2005 | Vuong et al. | |

OTHER PUBLICATIONS

Li, L. (1996). "Formulation and comparison of two recursive matrix algorithms for modeling layered diffraction gratings," *Journal of the Optical Society of America* A 13:1024-1035.

Haykin, S. (1999). *Neural Networks*. 2nd edition, M. Horton ed., Prentice Hall: Upper Saddle River, New Jersey, 9 pages (Table of Contents).

Ausschnitt, C. P. (Feb. 23, 2004). "A New Approach to Pattern Metrology." *Proceedings of SPIE* 5375:51-65.

* cited by examiner

*Primary Examiner*—Aditya Bhat
(74) *Attorney, Agent, or Firm*—Manuel B. Madriaga

(57) ABSTRACT

In allocating processing units of a computer system to generate simulated diffraction signals used in optical metrology, a request for a job to generate simulated diffraction signals using multiple processing units is obtained. A number of processing units requested for the job to generate simulated diffraction signals is then determined. A number of available processing units is determined. When the number of processing units requested is greater than the number of available processing units, a number of processing units is assigned to generate the simulated diffraction signals that is less than the number of processing units requested.

24 Claims, 5 Drawing Sheets

Figure 1:
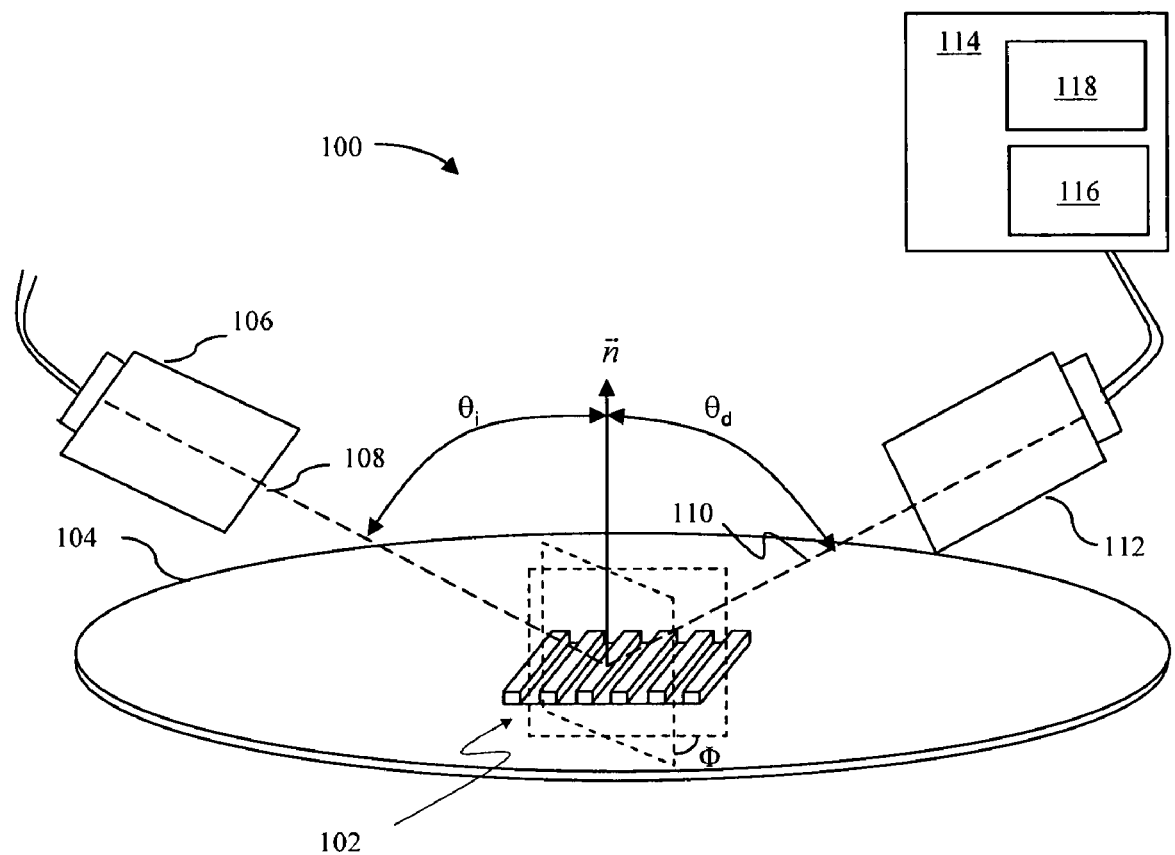

ALLOCATING PROCESSING UNITS TO GENERATE SIMULATED DIFFRACTION SIGNALS USED IN OPTICAL METROLOGY

CROSS REFERENCES TO RELATED APPLICATIONS

This application relates to U.S. patent application Ser. No. 11/525,793 entitled ALLOCATING PROCESSING UNITS TO PROCESSING CLUSTERS TO GENERATE SIMULATED DIFFRACTION SIGNALS, by Erva, et al., filed on Sep. 22, 2006, owned by the assignee of this application and incorporated herein by reference.

BACKGROUND

1. Field

The present application generally relates to optical metrology, and, more particularly, to allocating processing units in a computer system to generate simulated diffraction signals used in optical metrology.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional optical metrology system, the diffraction signal collected from illuminating the periodic grating (the measured-diffraction signal) is compared to one or more simulated-diffraction signals. Each simulated-diffraction signal is associated with a hypothetical profile. When a match is made between the measured-diffraction signal and one of the simulated-diffraction signals, the hypothetical profile associated with the simulated-diffraction signal is presumed to represent the actual profile of the periodic grating.

The simulated-diffraction signals used in optical metrology can be generated using a numerical analysis technique, such as rigorous coupled wave analysis (RCWA). More particularly, in the diffraction modeling technique, a simulated-diffraction signal is calculated based, in part, on solving Maxwell's equations. Alternatively, the simulated diffraction signals can be generated using a machine learning system (MLS). Generating the simulated diffraction signal, however, involves performing a large number of complex calculations, which can be time consuming and costly.

SUMMARY

In one exemplary embodiment, in allocating processing units of a computer system to generate simulated diffraction signals used in optical metrology, a request for a job to generate simulated diffraction signals using multiple processing units is obtained. A number of processing units requested for the job to generate simulated diffraction signals is then determined. A number of available processing units is determined. When the number of processing units requested is greater than the number of available processing units, a number of processing units is assigned to generate the simulated diffraction signals that is less than the number of processing units requested.

DESCRIPTION OF THE DRAWING FIGURES

Figure 3:
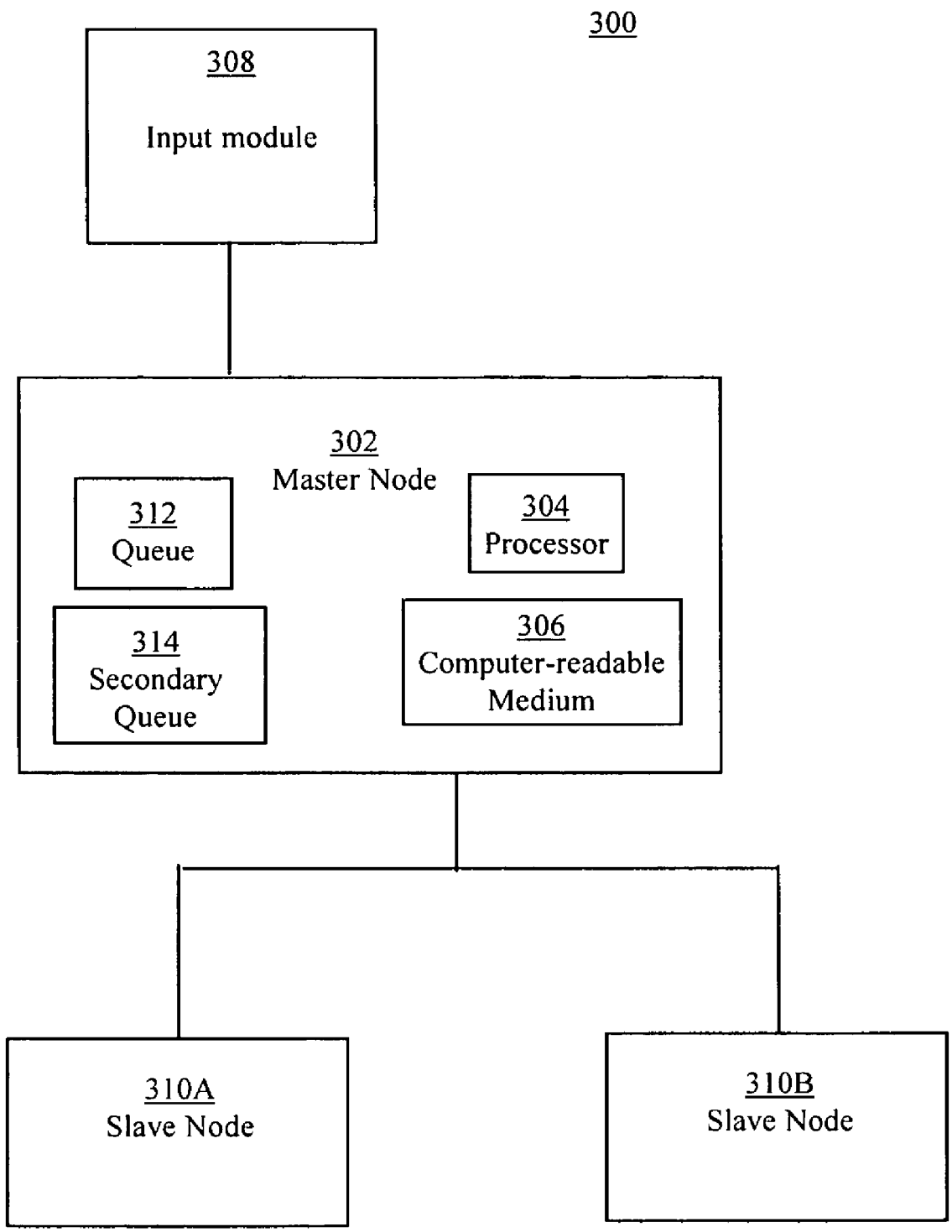
Figure 4:
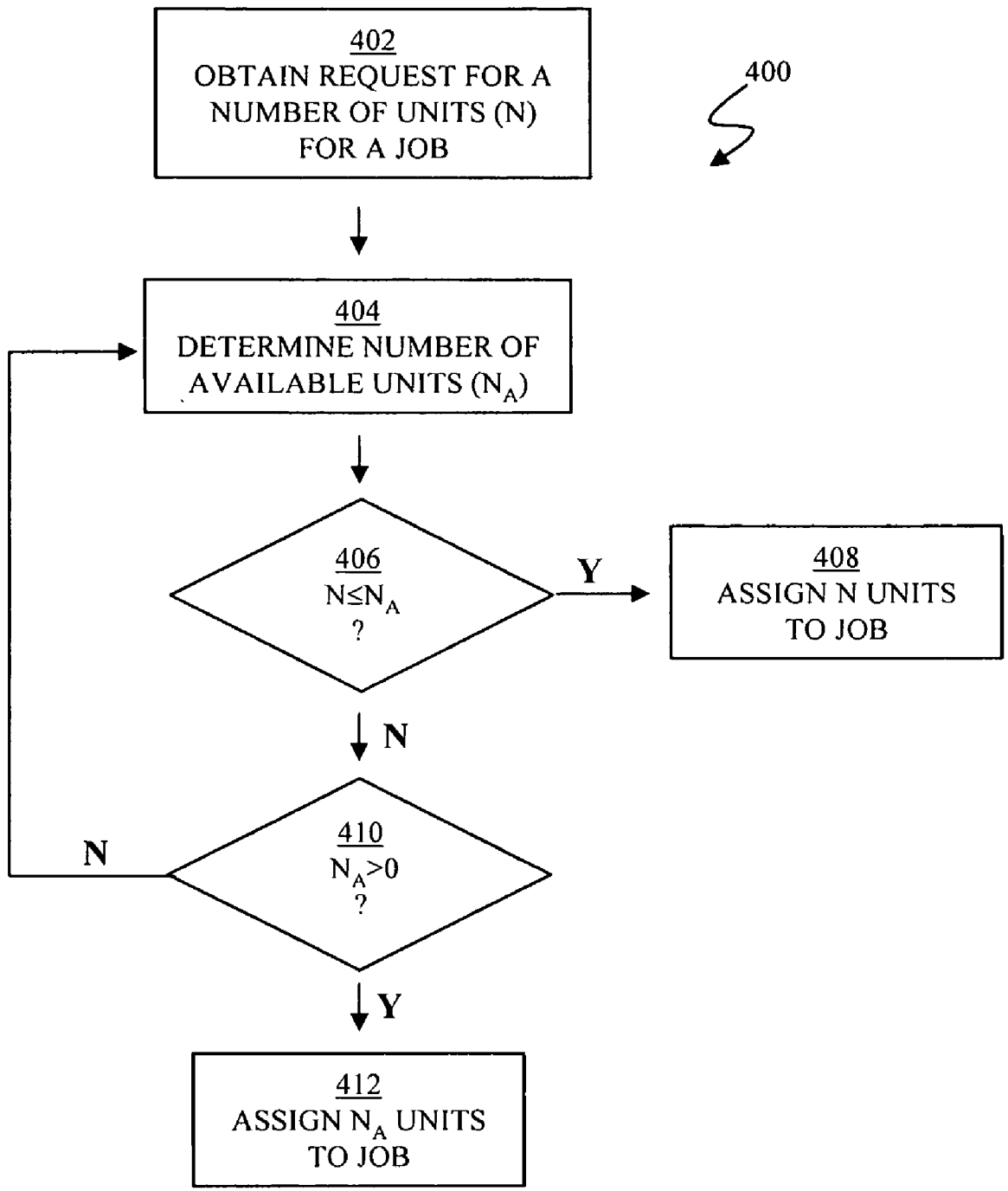
Figure 5:
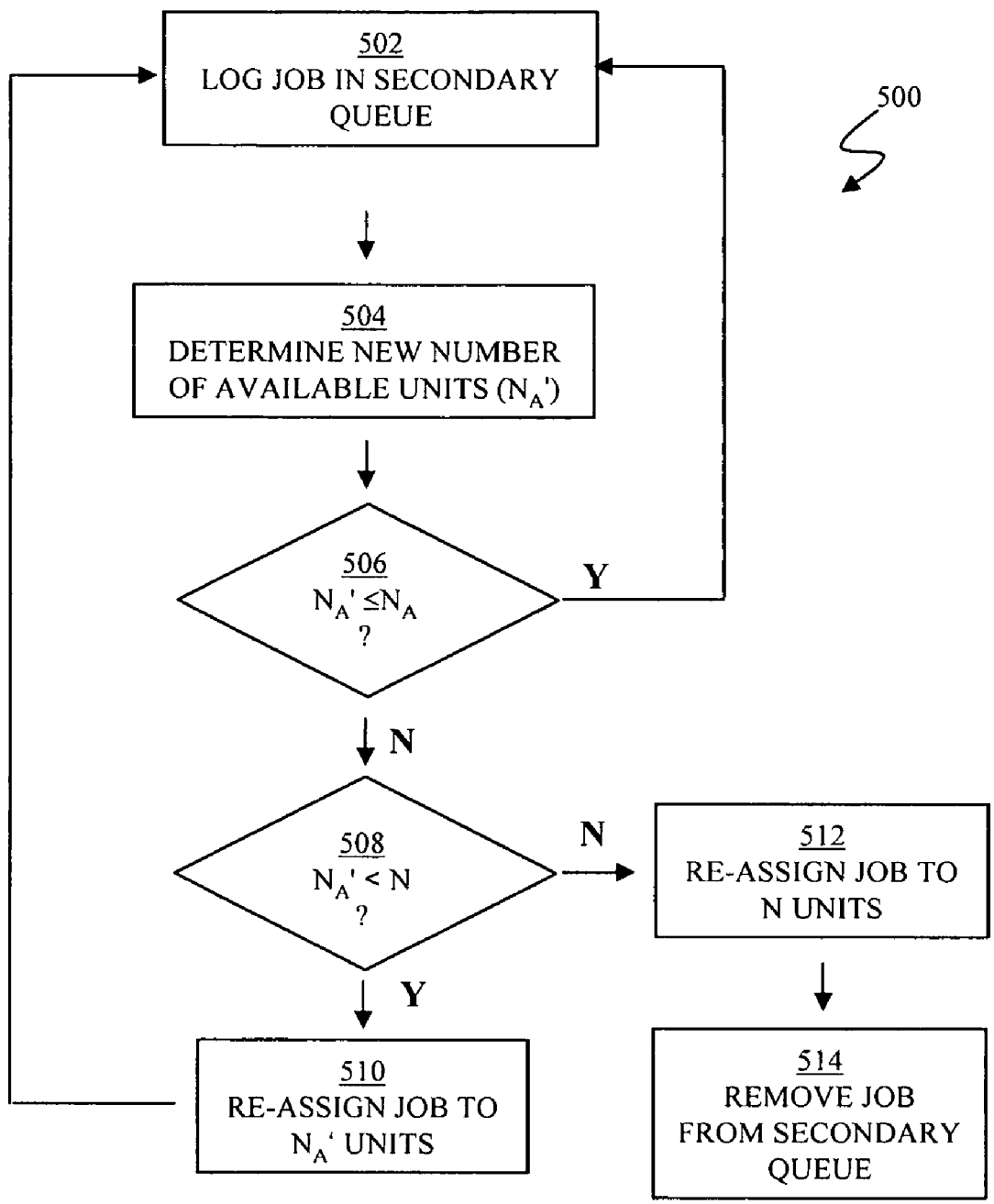

FIG. 1 depicts an exemplary optical metrology system;
FIGS. 2A-2E depict exemplary profile models;
FIG. 3 depicts an example of multiple processing units of a computer system;
FIG. 4 depicts a process for assigning a number of processing units to a job; and
FIG. 5 depicts a process for re-assigning a number of processing units to a job.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology Tools

With reference to FIG. 1, an optical metrology system 100 can be used to examine and analyze a structure formed on a semiconductor wafer 104. For example, optical metrology system 100 can be used to determine one or more features of a periodic grating 102 formed on wafer 104. As described earlier, periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1, optical metrology system 100 can include a photometric device with a source 106 and a detector 112. Periodic grating 102 is illuminated by an incident beam 108 from source 106. The incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, tan ($\Psi$), cos ($\Delta$), Fourier coefficients, and the like. Although a zero-order diffraction signal is depicted in FIG. 1, it should be recognized that non-zero orders can also be used. For example, see Ausschnitt, Christopher P., "A New Approach to Pattern Metrology," Proc. SPIE 5375-7, Feb. 23, 2004, pp 1-15, which is incorporated herein by reference in its entirety.

Optical metrology system 100 also includes a processing module 114 configured to receive the measured diffraction signal and analyze the measured diffraction signal. The processing module is configured to determine one or more features of the periodic grating using any number of methods which provide a best matching diffraction signal to the measured diffraction signal. These methods have been described elsewhere and include a library-based process, or a regression based process using simulated diffraction signals obtained by rigorous coupled wave analysis and machine learning systems.

2. Library-Based Process of Determining Feature of Structure

In a library-based process of determining one or more features of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing the profile of periodic grating 102 using a profile model. The profile model is characterized using a set of profile parameters. The profile parameters in the set are varied to generate hypothetical profiles of varying shapes and dimensions. The process of characterizing the actual profile of periodic grating 102 using profile model and a set of profile parameters can be referred to as parameterizing.

Figure 2A:
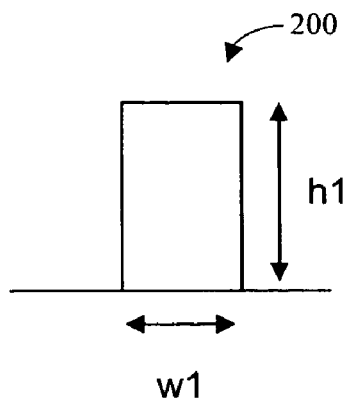
Figure 2B:
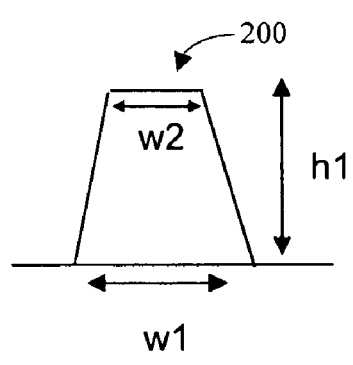
Figure 2C:
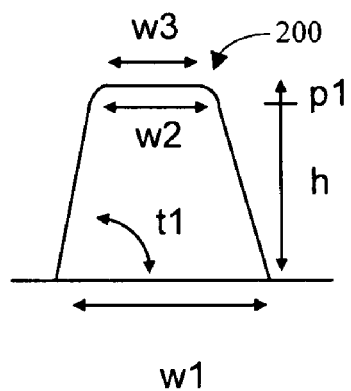
Figure 2D:
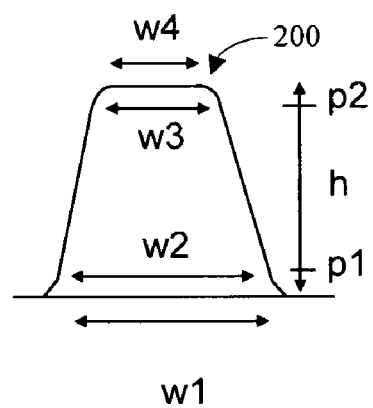
Figure 2E:
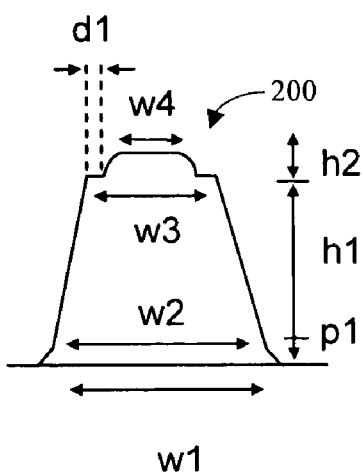

For example, as depicted in FIG. 2A, assume that profile model 200 can be characterized by profile parameters h1 and w1 that define its height and width, respectively. As depicted in FIGS. 2B to 2E, additional shapes and features of profile model 200 can be characterized by increasing the number of profile parameters. For example, as depicted in FIG. 2B, profile model 200 can be characterized by profile parameters h1, w1, and w2 that define its height, bottom width, and top width, respectively. Note that the width of profile model 200 can be referred to as the critical dimension (CD). For example, in FIG. 2B, profile parameter w1 and w2 can be described as defining the bottom CD (BCD) and top CD (TCD), respectively, of profile model 200.

As described above, the set of hypothetical profiles stored in library 116 (FIG. 1) can be generated by varying the profile parameters that characterize the profile model. For example, with reference to FIG. 2B, by varying profile parameters h1, w1, and w2, hypothetical profiles of varying shapes and dimensions can be generated. Note that one, two, or all three profile parameters can be varied relative to one another.

With reference again to FIG. 1, the number of hypothetical profiles and corresponding simulated diffraction signals in the set of hypothetical profiles and simulated diffraction signals stored in library 116 (i.e., the resolution and/or range of library 116) depends, in part, on the range over which the set of profile parameters and the increment at which the set of profile parameters is varied. The hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-Based Process of Determining Feature of Structure

In a regression-based process of determining one or more features of a structure, the measured diffraction signal is compared to a simulated diffraction signal (i.e., a trial diffraction signal). The simulated diffraction signal is generated prior to the comparison using a set of profile parameters (i.e., trial profile parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of profile parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, the processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. The subsequently generated simulated diffraction signal can be generated using an optimization algorithm, such as global optimization techniques, which includes simulated annealing, and local optimization techniques, which includes steepest descent algorithm.

The simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. As will be described below, the simulated diffraction signals can be generated by applying Maxwell's equations and using a numerical analysis technique to solve Maxwell's equations. It should be noted, however, that various numerical analysis techniques, including variations of RCWA, can be used.

In general, RCWA involves dividing a hypothetical profile into a number of sections, slices, or slabs (hereafter simply referred to as sections). For each section of the hypothetical profile, a system of coupled differential equations is generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the hypothetical profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Machine Learning Systems

The simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In one exemplary embodiment, the simulated diffraction signals in a library of diffraction signals, such as library 116 (FIG. 1), used in a library-based process are generated using a MLS. For example, a set of hypothetical profiles can be provided as inputs to the MLS to produce a set of simulated diffraction signals as outputs from the MLS. The set of hypothetical profiles and set of simulated diffraction signals are stored in the library.

In another exemplary embodiment, the simulated diffractions used in regression-based process are generated using a MLS, such as MLS 118 (FIG. 1). For example, an initial hypothetical profile can be provided as an input to the MLS to produce an initial simulated diffraction signal as an output from the MLS. If the initial simulated diffraction signal does not match the measured diffraction signal, another hypothetical profile can be provided as an additional input to the MLS to produce another simulated diffraction signal.

FIG. 1 depicts processing module 114 having both a library 116 and MLS 118. It should be recognized, however, that processing module 114 can have either library 116 or MLS 118 rather than both. For example, if processing module 114 only uses a library-based process, MLS 118 can be omitted. Alternatively, if processing module 114 only uses a regression-based process, library 116 can be omitted. Note, however, a regression-based process can include storing hypothetical profiles and simulated diffraction signals generated during the regression process in a library, such as library 116.

6. Allocating Processing Units to Generate Simulated Diffraction Signals

As noted above, generating simulated diffraction signals used in a library-based process or a regression-based process of optical metrology can be time consuming and costly. Thus, in one exemplary embodiment, the simulated diffraction signals are generated using multiple processors in a computer system. It should be recognized that the multiple processors can be multiple computers, multiple central processing units (CPU) within a computer, multiple-cores within a multi-core CPU, multiple execution threads on a hyper-threaded CPU/core, and the like.

For example, FIG. 3 depicts an example of a sever farm 300. In this example, server farm 300 is depicted as having a master node 302 and two slave nodes 310A, 310B. Master node 302 and slave nodes 310A, 310B of server farm 300 can be connected together using various well known network architectures. It should be recognized that server farm 300 can include any number slave nodes 310A, 310B. Additionally, server farm 300 can include multiple master nodes 302.

Master node 302 is typically configured as the control center for server farm 300. Slave nodes 310A, 310B are typically configured as clients, which receive instructions from master node 302. A user logs into master node 302 to submit a job to generate simulated diffraction signals. After the submitted job is received, master node 302 assigns the job to slave node 310A and/or slave node 310B depending on the number of processing units requested and the number of processing units (e.g., slave nodes 310A, 310B) available. The job is then run on the assigned slave nodes 310A, 310B, and, in particular, the processors in slave nodes 310A, 310B. In some cases, master node 302 may also be used to run a job requested by the user. Thus, the nodes of server farm 300 are used as processing units to run the job requested by the user.

The processing units (e.g., slave modes 310A, 310B) can generate the simulated diffraction signals using a numerical analysis technique, such as RCWA, or an MLS. For example, a profile model of a structure to be examined can be provided to one of the processing units. As described above, the profile model is characterized using a set of profile parameters. As also described above, one or more of the profile parameters of the profile model can be varied to generate a set of hypothetical profiles. Thus, the processing unit can be assigned a range of values for one or more profile parameters to be varied to generate an assigned set of hypothetical profiles. The process unit can then generate simulated diffraction signals corresponding to the set of hypothetical profiles using RCWA, MLS, and the like. It should be recognized that the process unit can be provided with the assigned set of hypothetical profiles rather than a profile model with an assigned range of values for one or more profile parameters.

Typically, master node 302 contains a processor 304 and a computer-readable medium 306. Master node 302 may be configured to receive a job requested through an input module 308. Input module 308 may be any component that allows the user to connect to master node 302 through a network, such as a network interface card. Alternatively, input module 308 may be a local terminal having a monitor, mouse and keyboard directly connected to master node 302 through which the user can request a job.

Server farm 300 can also include a queuing system to queue multiple jobs. FIG. 3 depicts a queue 312 of a queuing system as being resident on master node 302. It should be recognized, however, that queue 312 can be resident in various and multiple locations in server farm 300. It should also be recognized that the queuing system can queue multiple jobs according to various well known queuing algorithms.

FIG. 4 depicts an exemplary process 400 for allocating a number of processing units to a job to generate simulated diffraction signals. In step 402, a job to generate simulated diffraction signals is received. The received job specifies a number of requested processing units (N) to be used in performing the job. As described above, typically a user logs into a master node of a server farm, as depicted in FIG. 3, and submits the job. Typically, the user will determine the number of processing units needed for a particular job based on the size of the job (i.e., number of processing units required to complete the job) and how quickly the user would like to obtain the results. Other factors, which the user may take into account, include the scalability of the job (i.e., how much performance gain does the user get when they increase the number of processing units). It should be recognized, however, that the number of requested processing units can be automatically determined using an allocation algorithm.

As noted above, a queuing system can be used to queue multiple jobs. When a queuing system is used, the job request can include a priority specified by the user. The queuing system can then take into account the priorities specified in multiple jobs to queue the multiple jobs for processing by the server farm in accordance with a queuing algorithm. For example, when multiple jobs are in the queue, a job with a higher priority can be run before a job with a lower priority.

In step 404, the number of available processing units ($N_A$) is determined. The number of available processing units can be determined by determining the number of free processing units present in the computer system. Free processing units are processing units that are not processing a job. Additionally, when a queuing system is used with priorities specified for the jobs, availability can be determined based also on the priority of the requested job.

For example, if the requested job has a higher priority than a job currently running on one or more of the processing units, then the queuing system can make the one or more processing units of the lower priority job available to the requested job. As a further example, assume a user requests five processing units for a job on a multiple server farm containing six processing units. Assume also that three of the processing units are currently processing a job having a higher priority than the requested job. In this scenario, the queuing system determines that three processing units are available for the requested job. However, if three of the processing units are running a job having a lower priority than the requested job, then the queuing system may determine that all six of the processing units are available for the requested job. Thus, processing of the lower priority job is stopped at a checkpoint. The higher priority job is then performed. When the higher job is completed, the lower priority job is resumed starting at the last checkpoint.

In step 406, the number of requested processing units (N) is compared to the number of available processing units ($N_A$). If the number of requested processing units is less than or equal to the number of available processing units, then, in step 408, the number of requested processing units is assigned to the job. If the number of requested processing units is greater than the number of available processing units, then, in step 410, a determination is made as to whether the number of available processing units is greater than zero. If the number of available processing units is greater than zero, then, in step 412, the number of available processing units is assigned to the requested job. If the number of available processing units is zero, then steps 404-410 are repeated until the job gets assigned the number of requested processing units or the number of available processing units.

In one exemplary embodiment, when a queuing system is used, a priority can be specified such that when a job is obtained from the queue and the number of available processing units ($N_A$) is greater than the number of requested processing units (N) and the queue is empty after the job is obtained from the queue, the job is assigned the number of available processing units ($N_A$) rather than the number of requested processing units (N). For example, assume a job in the queue requests four processing units (i.e., N=4). Assume also that when this job is obtained from the queue to be run there are six available processing units (i.e., $N_A$=6) and the queue is empty. Thus, in the present exemplary embodiment, at step 408, six process units are assigned to run the job even though the job requested only four processing units.

With reference again to FIG. 3, in one exemplary embodiment, when a job has been assigned to less than the number of requested processing units (N), the job is logged in a secondary queue 314. When a new number of available processing units ($N_A'$) exceeds the previous number of available processing units ($N_A$), the job is re-assigned to the new number of available processing units ($N_A'$). The job remains in secondary queue 314 until it is assigned to the number of requested processing units (N). It should be recognized that secondary queue 314 can be maintained in various locations and formats. For example, secondary queue 314 can be maintained in computer-readable medium 306 of master node 302. Additionally, it should be recognized that queue 312 and secondary queue 314 can be portions of a single queue.

FIG. 5 depicts an exemplary process 500 for re-assigning a job that has been assigned to less than the number of requested processing units for the job. In step 502, the job is logged in a secondary queue. In step 504, a new number of available processing units ($N_A'$) is determined. In step 506, if the new number of available processing units ($N_A'$) is less than or equal to the previous number of available processing units ($N_A$), then the job continues to be logged in the secondary queue and steps 502 and 504 are repeated. In step 506, if the new number of available processing units ($N_A'$) exceeds the previous number of available processing units ($N_A$), then, in step 508, a determination is made as to whether the new number of available processing units ($N_A'$) is less than the number of requested processing units (N).

If the new number of available processing units ($N_A'$) is less than the number of requested processing units (N), then, in step 510, the job is re-assigned to the new number of available processing units ($N_A'$). Steps 502-508 are then repeated.

If the new number of available processing units ($N_A'$) is not less than the number of requested processing units (N), then, in step 512, the job is re-assigned to the requested number of processing units. In step 514, the job is removed from the secondary queue.

As an example, assume a server farm has six processing units and that a first job is being processed using three of the six processing units. Now assume a second job is received that requests five processing units. In this example, in accordance with process 400 (FIG. 4), the second job is assigned to the three available processing units rather than the requested five processing units. In step 502, because the second job was assigned to less processing units than requested, the second job is logged in the secondary queue.

Now assume that the first job is completed and the three processing units running the first job become available. The new number of available processing units is six, which includes the three processing units currently running the second job. In step 506, the new number of available processing units is determined to be greater than the previous number of available processing units. In step 508, the new number of available processing units is determined to be not less than the number of requested processing units. Thus, in step 512, the second job is re-assigned to the number of requested processing units (i.e., five processing units). In step 514, the second job is removed from the secondary queue.

With reference again to FIG. 3, the processor 304, of the master node 302, in FIG. 3, may be configured to perform the steps of process 400 (FIG. 4) and/or process 500 (FIG. 5). Additionally, process 400 (FIG. 4) and/or process 500 (FIG. 5) may be stored in the computer-readable medium 306 of the master node 302 as computer executable instructions, which can be executed by processor 304.

In one exemplary embodiment, the simulated diffraction signals generated by the multiple processing units can be used in optimizing a profile model of a structure formed on a wafer. In particular, an initial optical metrology model can be defined for a structure to be examined. Simulated diffraction signals can be generated for the initial optical metrology model using multiple processing units. The one or more simulated diffraction signals can be compared to a measured diffraction signal of the structure. The results of this comparison can be evaluated using one or more termination criteria, such as a cost function, goodness of fit (GOF), and the like. If the one or more termination criteria are not met, the initial optical metrology model can then be altered to generate a refined optical metrology model. The process of generating diffraction signals and comparing the diffraction signals to the measured diffraction signal can be repeated. This process of altering the optical metrology model can be repeated until the one or more termination criteria are met to obtain an optimized metrology model. For detailed description of metrology model optimization, refer to U.S. patent application Ser. No. 10/206,491, OPTIMIZED MODEL AND PARAMETER SELECTION FOR OPTICAL METROLOGY, by Vuong, et al., filed Jun. 27, 2002; and U.S. patent application Ser. No. 11/061,303, OPTICAL METROLOGY OPTIMIZATION FOR REPETITIVE STRUCTURES, by Vuong, et al., filed on Apr. 27, 2004, both of which are incorporated herein by reference in their entireties.

In another exemplary embodiment, the simulated diffraction signals generated by the multiple processing units can be used in a regression-based process of optical metrology. In particular, in a regression-based process, a measured diffraction signal of a structure can be compared to one simulated diffraction signal generated using one of the multiple processing units. If the diffraction signals do not match within a matching criterion, the measured diffraction signal can be compared to another simulated diffraction signal generated by another one of the multiple processing units. As noted above, the simulated diffraction signals used during the regression process can be stored in a dynamic library for subsequent use.

In still exemplary embodiment, the simulated diffraction signals generated by the multiple processing units can be used in a library-based process of optical metrology. In particular, in a library-based process, the simulated diffraction signals and hypothetical profiles corresponding to the simulated diffraction signals are stored in a library. A measured diffraction signal of a structure is then compared to one or more simulated diffraction signals stored in the library. The hypothetical profile corresponding to the best matching simulated diffraction signal is assumed to represent the profile of the structure.

In yet another exemplary embodiment, the multiple processing units can be used to optimize a profile model, perform a regression process using the optimized profile model, generate a library using the optimized profile model, then verify the generated library. In particular, as described above, simulated diffraction signals generated by the multiple processing units can be used to optimize a profile model. As also described above, the simulated diffraction signals generated by the multiple processing units can be used in a regression-based process. In the present embodiment, the regression-based process is performed using the profile model optimized using the simulated diffraction signals generated using the multiple processing units. It should be recognized that the simulated diffraction signals used in the regression-based process can be the same or different than the simulated diffraction signals used to optimize the profile model.

After performing the regression-based process, the simulated diffraction signals generated by the multiple processing units can be used to generate a library of simulated diffraction signals and hypothetical profiles. In the present exemplary embodiment, the hypothetical profiles in the library are generated based on the optimized profile model, and the simulated diffraction signals in the library are generated using the multiple processing units. It should be recognized that the simulated diffraction signals used to generate the library can be the same or different than the simulated diffraction signals used to perform the regression-based process and/or to optimize the profile model.

After the library is generated, the multiple processing units can be used to verify the generated library. For example, the generated library can be verified by obtaining a set of measured diffraction signals, and then comparing the set of measured diffraction signals to the simulated diffraction signals in the generated library to determine best matching diffraction signals. The multiple processing units can be used to expedite the process of comparing the set of measured diffraction signals to the simulated diffraction signals in the generated library.

Although exemplary embodiments have been described, various modifications can be made without departing from the spirit and/or scope of the present invention. Therefore, the present invention should not be construed as being limited to the specific forms shown in the drawings and described above.

We claim:

1. A method of utilizing computer-executable instructions for allocating processing units of a computer system to generate simulated diffraction signals in optical metrology, the computer system having a number of processing units, the method comprising:
   a) obtaining a request for a job to generate simulated diffraction signals using multiple processing units of the computer system;
   b) determining a number of requested processing units for the job to generate simulated diffraction signals;
   c) determining a number of available processing units; and
   d) when the number of requested processing units is greater than the number of available processing units, assigning a number of processing units to generate the simulated diffraction signals that is less than the number of requested processing units;
   e) determining a new number of available processing units;
   f) when the new number of available processing units exceeds the number of available processing units determined in c), re-assigning the job to the new number of available processing units or the number of requested processing units;
   g) if the number of available processing units is less than the number of requested processing units, re-assigning the job to the new number of available processing units; and
   h) if the number of available processing units is not less than the number of requested processing units, re-assigning the job to the number of requested processing units.

2. The method of claim 1, further comprising:
   after h), obtaining the simulated diffraction signals generated by the processing units; and comparing the obtained simulated diffraction signals to a measured diffraction signal of a structure formed on a wafer to optimize a profile model of the structure.

3. The method of claim 2, further comprising:
determining a profile of the structure in a regression process using the optimized profile model and simulated diffraction signals generated by the processing units.

4. The method of claim 3, further comprising:
generating a library of simulated diffraction signals and hypothetical profiles of the structure, wherein the hypothetical profiles are generated based on the optimized profile model, and wherein the simulated diffraction signals in the library are generated by the processing units.

5. The method of claim 4, further comprising:
verifying the generated library using the processing units.

6. The method of claim 1, further comprising:
after h), obtaining the simulated diffraction signals generated by the processing units; and
comparing the obtained simulated diffraction signals to a measured simulated diffraction signal of a structure formed on a wafer in a regression process to determine a profile of the structure.

7. The method of claim 1, further comprising:
after h), obtaining the simulated diffraction signals generated by the processing units; and
storing the obtained simulated diffraction signals and hypothetical profiles corresponding to the obtained simulated diffraction signals in a library.

8. The method of claim 1, further comprising:
when the number of processing units assigned to the job is less than the number of requested processing units, logging the job in a secondary queue; and
when the new number of available process units does not exceed the number of available processing units determined in h), maintaining the log of the job in the secondary queue.

9. The method of claim 8, further comprising:
after g), maintaining the log of the job in the secondary queue.

10. The method of claim 8, further comprising:
after h), removing the log of the job from the secondary queue.

11. The method of claim 1, further comprising:
when the number of requested processing units is greater than the number of available processing unit, determining if the number of available processing units is greater than zero;
if the number of processing units is determined to be zero, then iterating step c); and
if the number of processing units is determined to be greater than zero, then assigning the number of available processing units determined in c) to the job.

12. The method of claim 1, further comprising:
queuing jobs in a queue, wherein the job obtained in a) are obtained from the queue based on a priority assigned to the job;
when a first job is currently being processed, a second job is obtained from the queue with a higher priority than the first job currently being processed, and the number of requested processing units by the second job is greater than the number of available processing units:
stopping the first job at a checkpoint;
running the second job; and
when the second job is completed, resuming the first job at the checkpoint.

13. The method of claim 1, further comprising:
when the queue is empty after the job is obtained from the queue and the number of available process units is greater than the number of requested processing units by the job obtained from the queue, assigning the job the number of available processing units rather than the number of requested processing units by the job.

14. A computer-readable medium containing computer-executable instructions for allocating processing units of a computer system to generate simulated diffraction signals in optical metrology, comprising instructions for:
a) obtaining a request for a job to generate simulated diffraction signals using multiple processing units;
b) determining a number of requested processing units for the job to generate simulated diffraction signals;
c) determining a number of available processing units;
d) when the number of requested processing units is greater than the number of available processing units, assigning a number of processing units to generate the simulated diffraction signals that is less than the number of requested processing units;
e) determining a new number of available processing units;
f) when the new number of available processing units exceeds the number of available processing units determined in c), re-assigning the job to the new number of available processing units or the number of requested processing units;
g) if the number of available processing units is less than the number of requested processing units, re-assigning the job to the new number of available processing units; and
h) if the number of available process units is not less than the number of requested processing units, re-assigning the job to the number of requested processing units.

15. The computer-readable medium of claim 14, further comprising instructions for:
when the number of processing units assigned to the job is tess than the number of requested processing units, logging the job in a secondary queue; and
when the new number of available process units does not exceed the number of available processing units determined in c), maintaining the log of the job in the secondary queue.

16. The computer-readable medium of claim 15, further comprising instructions for:
after g), maintaining the log of the job in the secondary queue.

17. The computer-readable medium of claim 16, further comprising instructions for:
after h), removing the log of the job from the secondary queue.

18. The computer-readable medium of claim 14, further comprising instructions for:
when the number of processing units is greater than the number of available processing unit, determining if the number of available processing units is greater than zero;
if the number of processing units is determined to be zero, then iterating step c); and
if the number of processing units is determined to be greater than zero, then assigning the number of available processing units determined in c) to the job.

19. The computer-readable medium of claim 14, further comprising instructions for:
queuing jobs in a queue, wherein the job obtained in a) are obtained from the queue based on a priority assigned to the job;

when a first job is currently being processed, a second job is obtained from the queue with a higher priority than the first job currently being processed, and the number of requested processing units by the second job is greater than the number of available processing units:
stopping the first job at a checkpoint;
running the second job; and
when the second job is completed, resuming the first job at the checkpoint.

20. The computer-readable medium of claim 14, further comprising instructions for:
queuing jobs in a queue, wherein the job obtained in a) are obtained from the queue based on a priority assigned to the job;
when the queue is empty after the job is obtained from the queue and the number of available process units is greater than the number of requested processing units by the job obtained from the queue, assigning the job the number of available processing units rather than the number of requested processing units by the job.

21. The computer-readable medium of claim 14, further comprising instructions for:
after h), obtaining the simulated diffraction signals generated by the processing units;
comparing the obtained simulated diffraction signals to a measured diffraction signal of a structure formed on a wafer to optimize a profile model of the structure;
determining a profile of the structure in a regression process using the optimized profile model and simulated diffraction signals generated by the processing units;
generating a library of simulated diffraction signals and hypothetical profiles of the structure, wherein the hypothetical profiles are generated based on the optimized profile model, and wherein the simulated diffraction signals in the library are generated by the processing units; and
verifying the generated library using the processing units.

22. A system for allocating processing units of a computer system to generate simulated diffraction signals in optical metrology, the system comprising:
a plurality of processing units configured to generate simulated diffraction signals; and
a processor configured to:
obtain a request for a job to generate simulated diffraction signals using one or more of the plurality of processing units;
determine a number of requested processing units for the job;
determine a number of available processing units; and
when the number of requested processing units is greater than the number of available processing units, assign a number of processing units to the job that is less than the number of requested processing units;
determine a new number of available processing units;
when the new number of available processing units exceeds the number of available processing units, re-assign the job to the new number of available processing units or the number of requested processing units;
if the number of available processing units is less than the number of requested processing units, re-assign the job to the new number of available processing units; and
if the number of available process units is not less than the number of requested processing units, re-assign the job to the number of requested processing units.

23. The system of claim 22, further comprising:
a secondary queue,
wherein the processor is further configured to:
when the number of processing units assigned to the job is less than the number of requested processing units, log the job in the secondary queue; and
when the new number of available process units does not exceed the number of available processing units, maintain the log of the job in the secondary queue.

24. The system of claim 22, further comprising:
a library of simulated diffraction signals and hypothetical profiles of the structure, wherein the hypothetical profiles are generated based on the optimized profile model, and wherein the simulated diffraction signals in the library are generated by the processing units.

* * * * *